(12) United States Patent
Bourlon et al.

(10) Patent No.: US 12,680,995 B2
(45) Date of Patent: Jul. 14, 2026

(54) SYSTEMS AND METHODS FOR ESTIMATING AN EMISSION RATE OF A SOURCE

(71) Applicant: EOSENSE INC., Darmouth (CA)

(72) Inventors: Evelise Bourlon, Laggan (CA);
Nicholas R. Nickerson, Halifax (CA);
Colleen M. Gosse, Darmouth (CA);
David A. Risk, Antigonish Landing (CA)

(73) Assignee: EOSENSE INC., Darmouth (CA)

( * ) Notice: Subject to any disclaimer, the term of this patent is extended or adjusted under 35 U.S.C. 154(b) by 321 days.

(21) Appl. No.: 18/696,640

(22) PCT Filed: Oct. 6, 2022

(86) PCT No.: PCT/CA2022/051475
§ 371 (c)(1),
(2) Date: Mar. 28, 2024

(87) PCT Pub. No.: WO2023/056557
PCT Pub. Date: Apr. 13, 2023

(65) Prior Publication Data
US 2025/0003938 A1     Jan. 2, 2025

Related U.S. Application Data

(60) Provisional application No. 63/253,746, filed on Oct. 8, 2021.

(51) Int. Cl.
*G01N 33/00* (2006.01)
*G01M 3/22* (2006.01)
(Continued)

(52) U.S. Cl.
CPC .......... *G01N 33/0068* (2024.05); *G01M 3/26* (2013.01); *G01W 1/10* (2013.01); *G01M 3/22* (2013.01);
(Continued)

(58) Field of Classification Search
CPC ........... G01N 33/0068; G01N 33/0073; G01N 33/0062; G01N 33/0075; G01W 1/10; Y02P 90/84; Y02P 90/845
(Continued)

(56) References Cited

U.S. PATENT DOCUMENTS 5,742,053 A * 4/1998 Rekunyk ................ G01V 9/007
                                                    250/338.5
6,369,387 B1 4/2002 Eckles
(Continued)

FOREIGN PATENT DOCUMENTS

EP        0448360 A1     2/1991

OTHER PUBLICATIONS

Tierney A. Foster-Wittig et al., Estimation of point source fugitive emission rates from a single sensor time 1 series: A conditionally-sampled Gaussian plume reconstruction, Atmospheric Environment, May 21, 2015, pp. 101-109, vol. 115, Amsterdam, NL.
(Continued)

*Primary Examiner* — Peter J Macchiarolo
*Assistant Examiner* — John M Royston
(74) *Attorney, Agent, or Firm* — Denis Keseris; Gowling WLG (Canada) LLP

(57) ABSTRACT

Systems and methods for estimating an emission rate of at least one source are described. The system includes an anemometer, a gas sensor and a processor. The processor is configured to: receive a background concentration of the gas not affected by the at least one source and atmospheric stability 5 information associated with the sensing location;
(Continued)

Industrial site 200
Sensor 203
Plume 215
Emission source 211
Emission source 201
Plume 205 measure a set of parameters, including a concentration of a gas and a wind speed and wind direction; input the N sets of parameters, the position and height of the at least one source, the position and height of the gas sensor, the background concentration and dispersion parameters into a function relating the gas concentration to the wind 10 direction; and invert the function relating the gas concentration to the wind direction to obtain each source emission rate.

20 Claims, 7 Drawing Sheets

(51) Int. Cl.
   *G01M 3/26* (2006.01)
   *G01W 1/10* (2006.01)

(52) U.S. Cl.
   CPC ..... *G01N 33/0062* (2013.01); *G01N 33/0073* (2013.01); *G01N 33/0075* (2013.01); *Y02P 90/84* (2015.11); *Y02P 90/845* (2015.11)

(58) Field of Classification Search
   USPC ........................................ 73/19.01, 23.2, 40
   See application file for complete search history.

(56) References Cited

U.S. PATENT DOCUMENTS

| | | | |
|---|---|---|---|
| 8,125,626 B2 | 2/2012 | Furtaw | |
| 8,130,379 B1 | 3/2012 | Burba et al. | |
| 10,386,258 B1 | 8/2019 | Steele et al. | |
| 2004/0064254 A1 * | 4/2004 | Archibald | ............. G01V 9/007 |
| | | | 702/2 |
| 2010/0268480 A1 | 10/2010 | Prince | |
| 2011/0213554 A1 | 9/2011 | Archibald et al. | |
| 2016/0161456 A1 | 6/2016 | Risk et al. | |
| 2018/0045596 A1 | 2/2018 | Prasad et al. | |
| 2021/0255158 A1 | 8/2021 | Smith et al. | |

OTHER PUBLICATIONS

Salby, M. L. (1996), Fundamentals of atmospheric physics (p. 627 (4, 5, 11, 14)), San Diego: Academic.

Mitchell, J.A., and K. Timbre, 1979: Atmospheric stability class from horizontal wind fluctuation. Presented at 72nd Annual Meeting of Air Pollution Control Association, Cincinnati, OH; Jun. 24-29, 1979, II-p. 9.

Turner, D.B., 1970: Workbook of atmospheric dispersion estimates / D. Bruce Turner. National Air Pollution Control Administration Cincinnati, Ohio, vii, 84 p.

* cited by examiner

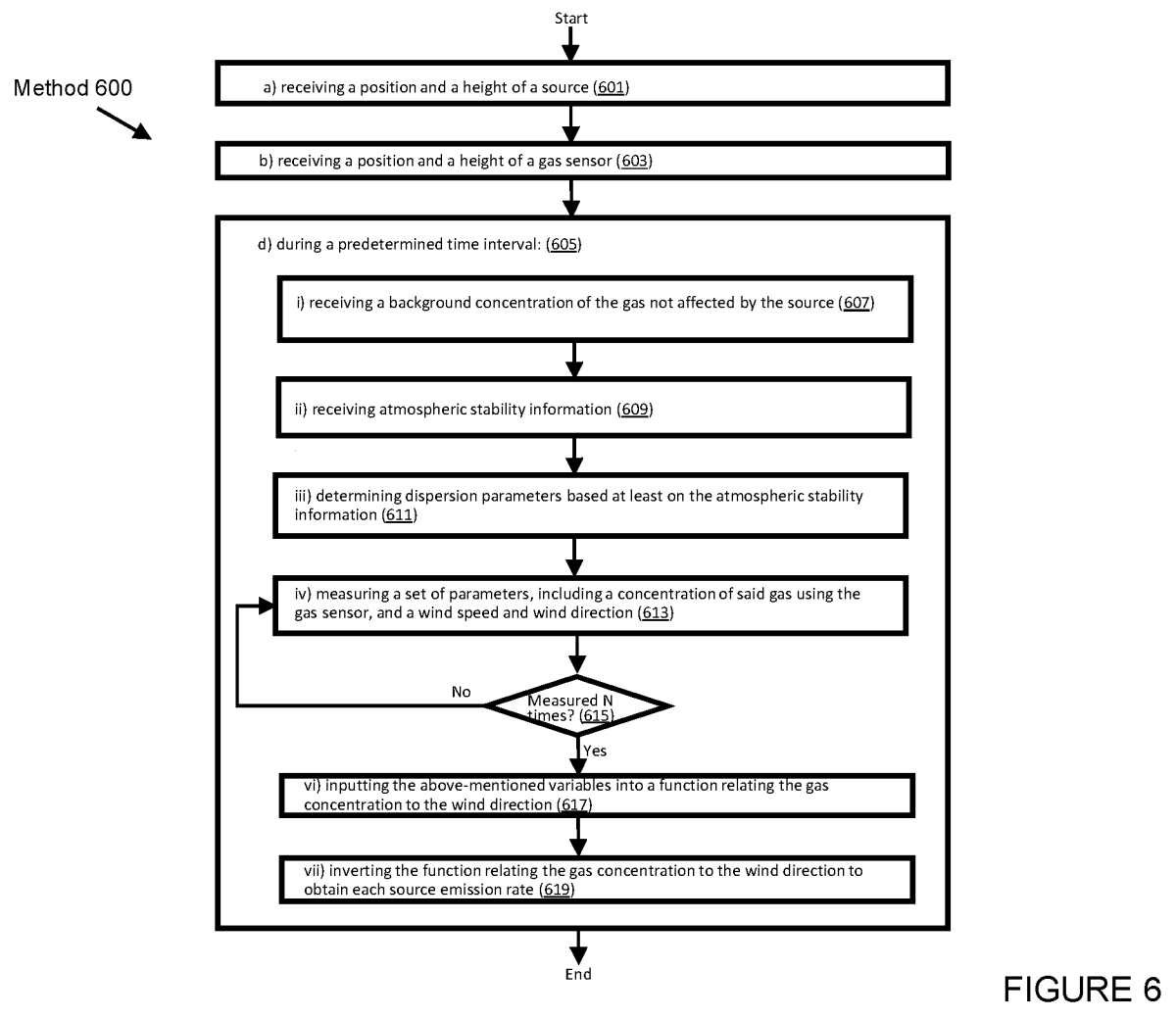

Method 600

Start a) receiving a position and a height of a source (601)

b) receiving a position and a height of a gas sensor (603)

d) during a predetermined time interval: (605)

i) receiving a background concentration of the gas not affected by the source (607)

ii) receiving atmospheric stability information (609)

iii) determining dispersion parameters based at least on the atmospheric stability information (611)

iv) measuring a set of parameters, including a concentration of said gas using the gas sensor, and a wind speed and wind direction (613)

Measured N times? (615)

No

Yes vi) inputting the above-mentioned variables into a function relating the gas concentration to the wind direction (617)

vii) inverting the function relating the gas concentration to the wind direction to obtain each source emission rate (619)

End

FIGURE 6

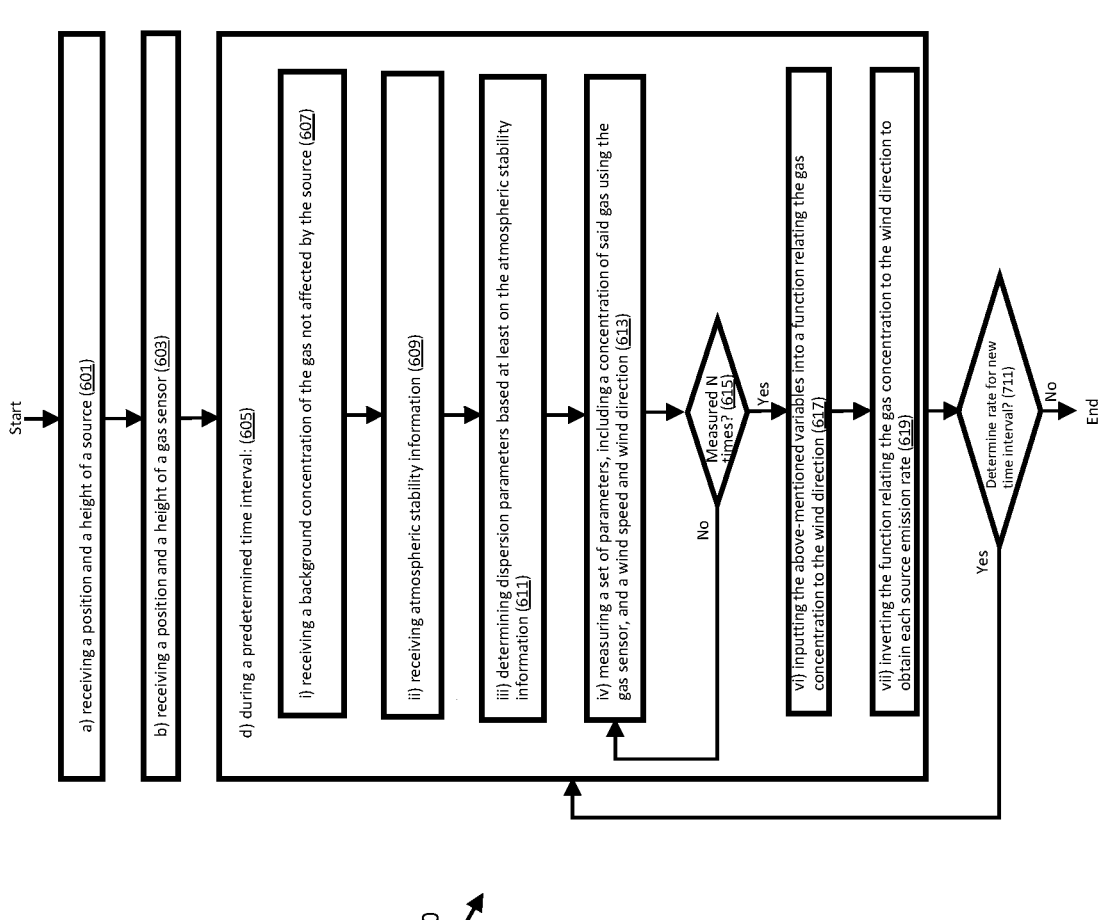

FIGURE 7

Method 700

Start a) receiving a position and a height of a source (601)

b) receiving a position and a height of a gas sensor (603)

d) during a predetermined time interval: (605)

i) receiving a background concentration of the gas not affected by the source (607)

ii) receiving atmospheric stability information (609)

iii) determining dispersion parameters based at least on the atmospheric stability information (611)

iv) measuring a set of parameters, including a concentration of said gas using the gas sensor, and a wind speed and wind direction (613)

Measured N times? (615)

No / Yes vi) inputting the above-mentioned variables into a function relating the gas concentration to the wind direction (617)

vii) inverting the function relating the gas concentration to the wind direction to obtain each source emission rate (619)

Determine rate for new time interval? (711)

Yes / No

End

Method 800

SYSTEMS AND METHODS FOR ESTIMATING AN EMISSION RATE OF A SOURCE

CROSS-REFERENCE TO RELATED APPLICATIONS

This non-provisional patent application is a U.S. National Phase of International Patent Application PCT/CA2022/051475 filed on Oct. 6, 2022 which is hereby incorporated by reference in its entirety and which claims priority from U.S. provisional patent application No. 63/253,746 filed on Oct. 8, 2021, which is incorporated herein by reference in its entirety.

FIELD OF THE DISCLOSURE

The present disclosure relates to systems and methods for monitoring gas emissions, and more particularly to systems and methods for determining an emission rate of at least one emission source.

BACKGROUND OF THE DISCLOSURE

Monitoring of gas emissions in many industrial sites, such as energy development sites, is of increasing commercial interest. For example, detection of gas emissions (e.g., methane, carbon dioxide, acetylene, carbon monoxide, hydrogen sulfide, etc.) can provide early warning indicators about the integrity of infrastructure and geological reservoirs.

Greenhouse gas emissions (GHGs) may come from industrial sources, such as manufacturing, agriculture, food processing, mining and construction facilities. GHGs can result from diverse processes, such as: on-site combustion of fossil fuels for heat and power; non-energy use of fossil fuels; chemical processes used in iron, steel, or cement production; and farming systems. GHGs are believed to be a significant contributor to global warming. GHGs that enter the atmosphere because of human activities can include: carbon dioxide, methane, nitrous oxide, and fluorinated gases such as hydrofluorocarbons, perfluorocarbons, and sulfur hexafluoride. Many governments are taking steps to reduce GHG emissions through policies that include the introduction of emissions trading programs, voluntary programs, carbon or energy taxes, and regulations and standards on energy efficiency and emissions. Because of this increase scrutiny on GHG emissions, many organizations track and/or try to minimize their GHG emissions. In some instances, many organizations may be required to do so by government regulations.

To address environmental concerns, "carbon credits" have been created on an international scale to provide a basis for organizations to control their GHG emissions. Emissions trading programs have created a market in which organizations can trade in "carbon credits." Thus, organizations can create an additional source of revenues by reducing their GHG emissions. For example, an organization may be incentivized to reduce its GHG emissions to gain carbon credits, and then sell those credits.

Any attempt to measure and/or reduce GHG emissions should be informed by precise and site-specific data. One of the problems associated with known devices and methods for monitoring gas emissions (such as for example, emission measuring equipment mounted on vehicles) is that they are typically arranged to take sporadic samples or "snapshots" of emissions at a given time.

Accordingly, known systems do not take into account variability in emissions caused by, for example, environmental factors (e.g., rain, wind, etc.). As such, knows devices and methods need to be deployed at the right time in order to take meaningful measurements. This requires a great deal of knowledge about the site being monitored and the environmental conditions during the monitoring process.

Furthermore, other variable processes associated with industrial sites, such as for example compressor venting, may add a further component of time to the emissions outside of that related to the environment. For example, a planned and controlled venting of natural gas to remove any air inside pipes of an industrial station may lead to emission measurements that suggest action be taken, despite such measurements not being representative of the actual longer-term behavior of the industrial site. Such temporal processes may lead to false negative/positive emission assessments.

Accordingly, there is a clear need to provide systems and methods for estimating emission rates of at least one source that do not fall foul of the above technical disadvantages.

SUMMARY OF THE DISCLOSURE

The following summary is intended to introduce the reader to the more detailed description that follows, and not to define or limit the claimed subject matter.

The present disclosure generally relates to systems and methods for estimating an emission rate of at least one source using measurements of gas concentration, wind speed and wind direction.

According to one aspect of the disclosure, there is provides a method for estimating an emission rate of at least one source, including:

a) receiving a position and a height of the at least one source;

b) receiving a position and a height of a gas sensor at a sensing location;

c) during a predetermined time interval:

i) receiving a background concentration of the gas not affected by the at least one source;

ii) receiving atmospheric stability information associated with the sensing location;

iii) determining dispersion parameters based at least on the atmospheric stability information;

iv) measuring a set of parameters, including:
a concentration of the gas using the gas sensor, and a wind speed and wind direction;

v) repeating step iv) N times during the predetermined time interval to collect N sets of parameters;

vi) inputting the N sets of parameters, the position and height of the at least one source, the position and height of the gas sensor, the background concentration of the gas not affected by the at least one source and the dispersion parameters into a function relating the gas concentration to the wind direction; and vii) inverting the function relating the gas concentration to the wind direction to obtain each source emission rate In some embodiments, the method includes repeating the steps i) to vii) for plurality of time intervals.

In some embodiments, the method further includes:
repeating step iv) to measure a new set of parameters;
inputting the new set of parameters, N−1 most recent prior sets of parameters, the position and height of the at least one source, the position and height of the inlet of the gas sensor, the background concentration of the gas not affected by the at least one source and the dispersion parameters into the function relating the gas concentration to the wind direction; and inverting the function relating the gas concentration to the wind direction to obtain each source new emission rate.

In some embodiments, the method further includes receiving the position and the height of the at least one source and the position and the height of the gas sensor by using a location awareness system.

In some embodiments, the method further includes using a linear solver to invert the function relating the gas concentration to the wind direction.

In some embodiments, the linear solver includes a linear least-square solver.

In some embodiments, the method further includes measuring the wind speed and the wind direction using a wind sensor.

In some embodiments, the wind sensor includes an anemometer.

In some embodiments, the position and the height of the at least one source is received from a Global Positioning System (GPS) device.

In some embodiments, the position of the gas sensor is received from a GPS device.

In some embodiments, receiving the position and the height of the gas sensor includes receiving the position and the height of an inlet of the gas sensor, wherein the gas sensor is adapted to receive, through the inlet into a chamber, ambient air containing the gas at the sensing location, and measure concentration of the gas inside the chamber.

According to another aspect of the disclosure, there is provided a system for estimating an emission rate of at least one source, including:

an anemometer for gauging wind direction and a wind speed;

a gas sensor for measuring concentration of a gas; and a processor coupled to the wind sensor and the gas sensor, the processor configured to:

a) receive a position and a height of the at least one source;

b) receive a position and a height of the gas sensor at a sensing location;

c) during a predetermined time interval:

i) receive a background concentration of the gas not affected by the at least one source;

ii) receive atmospheric stability information associated with the sensing location;

iii) determine dispersion parameters based at least on the atmospheric stability information;

iv) measure a set of parameters, including:
a concentration of the gas using the gas sensor, and
a wind speed and wind direction using the wind sensor;

v) repeat step iv) N times during the interval to collect N sets of parameters;

vi) input the N sets of parameters, the position and height of the at least one source, the position and height of the gas sensor, the background concentration of the gas not affected by the at least one source and the dispersion parameters into a function relating the gas concentration to the wind direction; and vii) invert the function relating the gas concentration to the wind direction to obtain each source emission rate.

In some embodiments, the processor is further configured to repeat the steps i) to vii) for plurality of time intervals.

In some embodiments, the processor is further configured to:

repeat step iv) to measure a new set of parameters;

input the new set of parameters, N−1 most recent prior sets of parameters, the position and height of the at least one source, the position and height of the inlet of the gas sensor, the background concentration of the gas not affected by the at least one source and the dispersion parameters into the function relating the gas concentration to the wind direction; and invert the function relating the gas concentration to the wind direction to obtain each source new emission rate.

In some embodiments, the processor is further configured to receive the position and the height of the at least one source and the position and the height of the gas sensor from a location awareness system.

In some embodiments, the processor is configured to invert the function relating the gas concentration to the wind direction by using a linear solver.

In some embodiments, the linear solver includes a linear least-square solver.

In some embodiments, the position and the height of the at least one source is received from a GPS device.

In some embodiments, the position of the gas sensor is received from a GPS device.

In some embodiments, the processor is configured to receive the position and the height of an inlet of the gas sensor, wherein the gas sensor is adapted to receive, through the inlet into a chamber, ambient air containing the gas at the sensing location, and measure concentration of the gas inside the chamber.

BRIEF DESCRIPTION OF THE DRAWINGS

In order that the claimed subject matter may be more fully understood, reference will be made to the accompanying drawings, in which:

FIG. 6 shows a flowchart of a method for determining an emission rate according to one example;

FIG. 7 shows a flowchart of a method for determining an emission rate according to another example.

DETAILED DESCRIPTION OF THE DISCLOSURE

Figure 1:
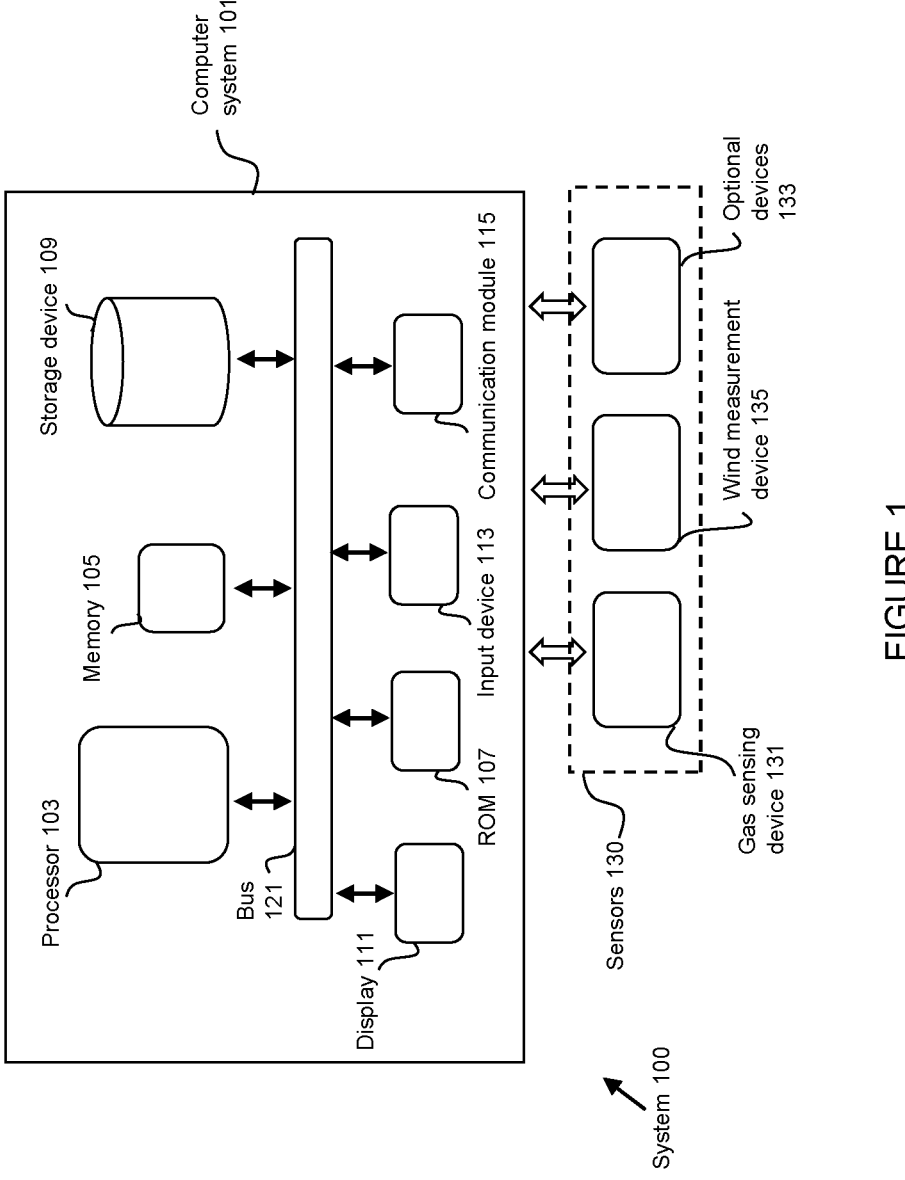
FIG. 1 shows a block diagram of a system for estimating an emission rate of at least one source according to one example.

It will be appreciated that, for simplicity and clarity of illustration, where considered appropriate, reference numerals may be repeated among the FIGURES to indicate corresponding or analogous elements or steps. In addition, numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description is not to be considered as limiting the scope of the claimed subject matter in any way but rather as merely describing the implementation of the various embodiments described herein.

"Concentration of a gas" as used herein refers to a quantifiable amount of a specific molecule, compound, or isotope in the atmosphere. For example, concentration of a gas may be as expressed in the parts-per notation (e.g., ppm, ppb).

"Gas emission" as used herein refers to a presence of one or more gases at a site (for e.g., an industrial site). The presence of such gas emissions may be intended (e.g., produced an industrial site during the normal operation of the site). Alternately, the presence of such gas may be unintended (e.g., produced at the industrial site because of abnormal operation of the industrial site). Abnormal operation of an industrial site my include, but is not limited to, operating the site with equipment that is defective or operating the site outside of government-regulated parameters. Intervention can include further investigation by the site operator, identification of one or more potential emission sources of the gas emission or controlling of one or more potential emission sources.

"Industrial site" herein refers to a geographically bounded region in which a plurality of gas emission sources are located and in which emission of gases in the air are to be monitored.

"Gas emission source" as used herein refers to any element located on the industrial site that can emit gas at a level that, alone or in conjunction with another emission source, can cause a gas emission.

"Location awareness system" as used herein refers to any hardware and/or software useful for determining/estimating the position of an object (e.g., an emission source, a gas sensor, etc.) with respect to one or more further objects (e.g., emission sources, a gas sensor, etc.) in a geographic area. Location awareness systems include, but are not limited to, hardware/software for geolocation using a Global Positioning System ("GPS"), an electronic compass, cellular base station triangulation, proximity awareness based on, e.g., WiFi signal strength, and/or any other location systems and/or methods. For example, location information provided by the location awareness system may include orientation (e.g., cardinal direction) and/or position information (e.g., coordinates of the Geographic Coordinate System or the Universal Transverse Mercator) relative to a predetermined position and/or a target (e.g., position of a gas sensor relative to an emission source, etc.), motion tracking (e.g., using inertial sensors) or the like, and any other positional information required by the systems disclosed herein for carrying out the methods disclosed herein.

GHG emissions can be present at all stages in the oil and gas value chain from production to processing to transmission and to distribution. In particular, on upstream oil and gas facilities, GHG emissions can come from flaring, equipment leaks, venting, and combustion. Understanding where these emissions are and the magnitude of the emissions can inform repairs and prioritize reductions. Emissions may be intentional or unintentional and many regulations differentiate between regulations from different industrial processes. There is increased scrutiny from governments, financial institutions and the general public for many industries to reduce their GHG emissions. For an organization to successfully reduce their emissions, it is imperative for organizations to understand their emissions.

The discussed elsewhere herein, the challenges with prior art methods of estimating gas emission rates include: many methods only capture a single point in time (i.e., aerial and vehicle based surveys), some methods cannot be used during winter weather conditions (i.e., optical gas imaging), some methods do not offer a detection limit suitable to meet regulatory requirements in some jurisdictions (satellite), and many methods do not quantify the emission rate or use emission factors to estimate an emission rate which are based on limited data and do not accurately represent many sites.

Many industrial emissions are highly variable, particularly those associated with processes on site and those that are affected by different weather conditions. Additionally, many industrial facilities are located in areas where sub-zero temperatures are common and prior art methods that are not suitable in these conditions limits when measurements can be taken.

The methods and systems described herein are directed to providing measurements with early reporting that allows for an accurate site understanding and interventions which will result in emissions reductions.

Referring to FIG. 1, there is a block diagram that illustrates a system 100 for estimating an emission rate of at least one source. The emission rate estimation system 100 can include a computer system 101 (or device). The methods and modules described in the present subject matter can be implemented using the computer system as a standalone device or on a distributed network of shared computer processing resources such as a cloud computing network. For example, a non-transitory computer-readable medium can be provided in which a computer program is stored for causing a computer to perform the disclosed method for estimating an emission rate of at least one source.

The system 100 can also include sensors 130. The sensors 130 can include a gas sensing device 131 (or gas sensor), a wind measurement device 135 (for e.g., anemometer, etc.) and/or optional devices 133 adapted to sense gas, location and wind parameters. For example, the sensors 130 may not include the optional devices. For example, the optional device may include a Global Positioning System (GPS) device. For example, the gas sensing device 131, the wind measurement device 135 and the optional device 133 can be integrated into a single computer system.

In another embodiment, the computer system as described above can be integrated into a gas sensing device to perform the method for estimating an emission rate of at least one source as described in the present disclosure. In a further embodiment, the GPS device and/or the wind measurement device can also be integrated into the gas sensing device.

Referring to back FIG. 1, the computer system 101 can include a bus 121 or other communication mechanism for communicating information, and a processor 103 coupled with bus 121 for processing information. In various embodiments, the computer system 121 can also include a memory, which can be a random-access memory (RAM) 105 or other dynamic storage device, coupled to bus 121 for determining instructions to be executed by processor 103. Memory also can be used for storing temporary variables or other intermediate information during execution of instructions to be executed by processor 103.

In various embodiments, the computer system 101 can further include a read only memory (ROM) 107 or other static storage device coupled to bus 121 for storing static information and instructions for processor 103. A storage device 109, such as a magnetic disk or optical disk, can be provided and coupled to bus 121 for storing information and instructions. In various embodiments, the computer system 101 can be coupled via bus 121 to a display 111, for displaying information to the system/computer user. An input device 113, including alphanumeric and other keys, can be coupled to bus 121 for communicating information and command selections to processor 103. The computer system 101 can further include a communication module 115 configured to connect and communicate data to and from the sensors 130.

Consistent with certain implementations of the present disclosure, results can be provided by computer system 101 in response to processor 103 executing one or more sequences of one or more instructions contained in memory 105. Such instructions can be read into memory 105 from another computer-readable medium or computer-readable storage medium, such as storage device 109. Execution of the sequences of instructions contained in memory 105 can cause processor 103 to perform the modules and methods/processes described herein. Alternatively, hard-wired circuitry can be used in place of or in combination with software instructions to implement the present teachings. Thus, implementations of the present teachings are not limited to any specific combination of hardware circuitry and software.

The term "computer-readable medium" (e.g., data store, data storage, etc.) or "computer-readable storage medium" as used herein refers to any media that participates in providing instructions to processor 103 for execution. Such a medium can take many forms, including but not limited to, non-volatile media, volatile media, and transmission media.

In addition to computer readable medium, data can be provided as signals on transmission media included in a communications apparatus or system to provide sequences of one or more instructions to processor 103 of computer system 101 for execution. For example, a communication apparatus may include a transceiver having signals indicative of instructions and data. The instructions and data are configured to cause one or more processors to implement the functions outlined in the disclosure herein, such as the method for estimating an emission rate of at least one source. Representative examples of data communications transmission connections can include, e.g., telephone modem connections, wide area networks (WAN), local area networks (LAN), infrared data connections, NFC connections, etc.

With reference to FIG. 1, the system 100 includes a gas sensing device 131 for measuring a concentration of a gas. The gas sensing device can include a temperature-controlled and/or moisture-controlled enclosure. The enclosure can have at least one inlet for receiving ambient air containing a gas surrounding the enclosure such that the gas sensing device performs measurements of gas concentration inside the enclosure. The inlet can provide fluid communication between the outside of the enclosure and the interior of the enclosure. The inlet may have fans mounted onto the walls of the enclosure for drawing air into the interior of the enclosure. The fans may also assist in controlling temperature of the enclosure, such as by drawing cooler ambient air into the interior of the enclosure. The fans may be controlled to turn on when the temperature within the enclosure exceeds a predetermined threshold, such as 25 degrees Celsius.

The gas sensing device can include at least one gas analyzer (for e.g., an open-path or a closed-path gas analyzer). For example, the gas analyzer can be a NDIR based analyzer, a laser-based analyzer, a chemical-based analyzer, etc. Specific gas analyzers can include, but are not limited to, the LI-7200 gas analyzer and the LI-7500 gas analyzer, both from LI-COR™ Biosciences™, as described in U.S. Pat. Nos. 6,369,387, 8,125,626 and 8,130,379, which disclose various useful features of open and closed path gas analyzers.

The gas analyzer can be operable to measure the concentration of at least one type of gas. The gas analyzer can also measure the concentration of two or more types of gas. For example, the gas analyzer can measure the concentration of two or more types of gas as long as they are not contaminating each other. Examples of types of gas can include methane, carbon dioxide, acetylene, carbon monoxide, hydrogen sulfide, etc.

The gas analyzer can generate data relating to measurements of concentrations of the gas. The gas sensing device can be in electronic communication with the computing system 101 to transmit data collected by the gas analyzer to the computing system.

The gas analyzer can be implemented as one or more multi-gas analyzer. The multi-gas analyzer refers to any gas analyzer that is operable to measure the concentration of one or more types of gas within a single device. For example, the gas analyzer can be a gas tracer, such as Picarro G2301, G2401, G2132-1 analyzers.

The gas sensing device can be placed at a stationary location within an industrial site to be monitored. For example, the gas sensing device can be placed at an industrial site to monitor the emission rate of one or more emission sources.

The gas sensing device can also be deployed on a mobile platform. For example, the gas sensing device can be moved around or transported on the mobile platform, such that the gas sensing device is moved to different locations. For example, the mobile platform stays stationary while the gas sensing device measures the concentrations of one or more types of gas. For example, the mobile platform can be a vehicle. The term "vehicle" can refer to a platform that is operable to move the gas sensing to at least two different locations within an industrial site. The vehicle may be a land-based vehicle, such as a car, truck, all-terrain vehicle, motorcycle, snowmobile, etc.

Referring to FIG. 1, the system 101 includes an optional device 133. For example, the optional device can be a GPS device. The GPS device can be in electronic communication with the system 101 to transmit positioning data to the computing system. For example, the positioning data can include a current location of the gas analyzer. For example, the positioning data can include a current location of the inlet of the gas analyzer at the time a concentration of a gas is measured by the gas analyzer. The GPS device can be positioned near the gas analyzer for tracking position of the gas analyzer.

The gas analyzer can be placed at a stationary location within an industrial site to be monitored. In this situation, the location of the gas analyzer relative to each source may be known and the GPS device may not be needed.

Referring to FIG. 1, the system 100 includes a wind measurement device 135. The wind measurement device can be in electronic communication with the computing system 101 to transmit wind data (for e.g., wind speed, wind direction, etc.) to the computing system. The wind measurement device can include, for example, an anemometer. The anemometer can, for example, include a device (e.g., digital compass) for measuring wind direction within a coordinate system such as the Universal Transverse Mercator (UTM) system. Alternatively, if the spatial orientation of the anemometer is determined, the anemometer can simply measure wind direction with respect to its own orientation and the method of the present disclosure can use the determined orientation and relative wind direction in estimating the emission rate(s).

The wind measurement device can measure wind speed (for e.g., the horizontal wind components) and wind direction in proximity to the location of the gas analyzer. For example, the wind measurement device can measure wind speed and wind direction at the time a concentration of a gas is measured by the gas analyzer. For example, the wind measurement device and the gas sensing device are synchronized to measure at the same time wind speed, wind direction and gas concentration.

Figure 2:
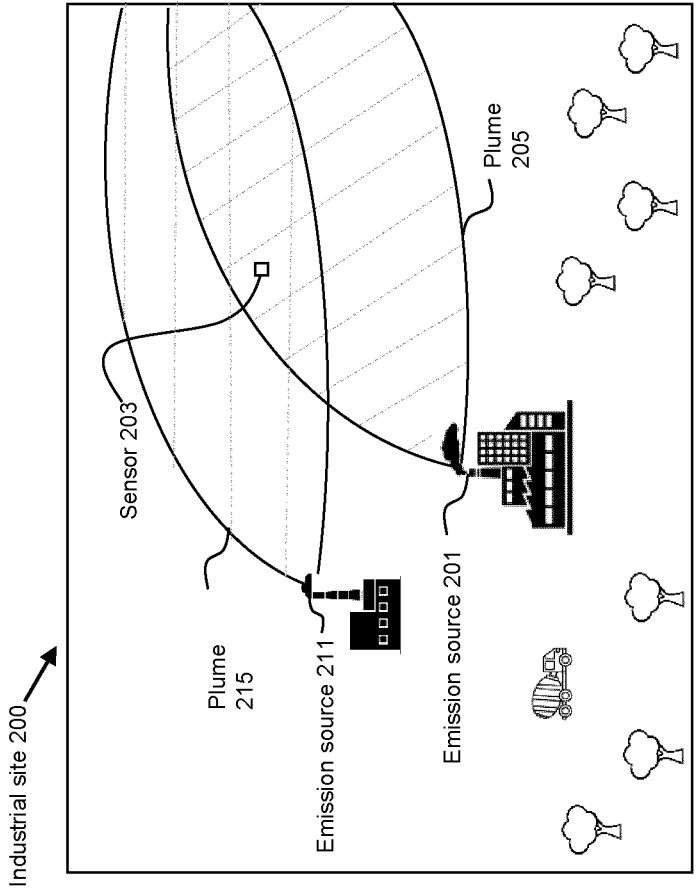
FIG. 2 shows a diagram of an industrial site according to one example.

Referring to FIG. 2, there is shown a first emission source 201 and a second emission source 211 located at an industrial site 200. The first emission source 201 emits a gas into the atmosphere from a chimney. The gas emitted by the source 201 disperses with the air parcels of the wind and other environmental conditions and takes on the form of a plume 205. A sensor 203 is located on the path of the plume 205. The sensor can be adapted to receive, through an inlet into a sensor chamber, ambient air containing a gas such that the sensor measures concentration of the gas inside the chamber. For example, the sensor 203 can also be configured to both measure wind and gas parameters.

In one embodiment, the sensor 203 can include a GPS device, a wind measurement device and a gas sensing device (e.g., gas analyzer). The gas sensing device can measure a concentration of the gas emitted by the source 201. The wind measurement device can measure wind speed and wind direction at the time a concentration of the gas is measured by the gas sensing device. The measured wind direction and the wind speed are representative of the direction and speed of the wind at the location of the gas sensing device. Data pertaining to the wind direction and the wind speed generated by the wind measurement device may be received at a computing system.

The second emission source 211 also emits a gas into the atmosphere from a chimney. The gas emitted by the source 211 disperses with the wind and other environmental conditions and takes on the form of a plume 215. The sensor 203 is also located on the path of the plume 215 to measure wind and gas parameters included therein. The gas sensing device can also measure a concentration of the gas emitted by the source 211. For example, the gas sensing device can measure the sum of the concentrations of the gas emitted by sources 201 and 211. The wind measurement device can measure wind speed and wind direction at the time the concentration of the gas emitted by the source 201 or 211 is measured by the gas sensing device.

Figure 3:
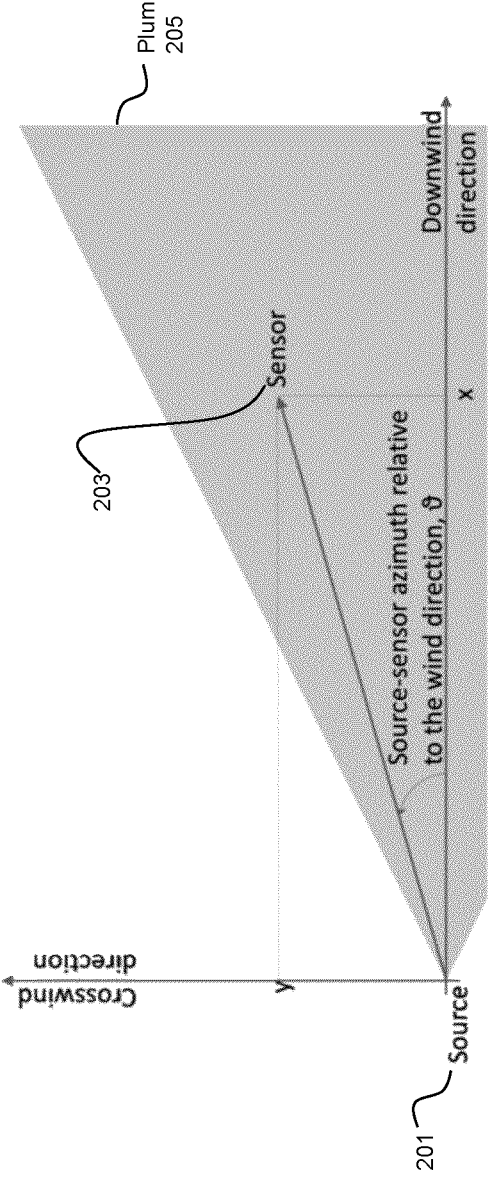
FIG. 3 shows a diagram of a source and a sensor positioned within a wind direction reference frame according to one example.

Referring to FIG. 3, there is shown an emission source 201, a sensor 203 and a plume 205 corresponding to the emission source 201 in a wind direction reference frame. The x-axis represents the downwind direction, and the y-axis represents the crosswind direction. The angle $\upsilon$ represents the source-sensor azimuth relative to the wind direction. The source-sensor azimuth u varies with wind direction (that can vary with time) as if the sensor was moving through a stationary plume.

Referring to FIG. 6, there is shown a method 600 for estimating an emission rate of one or more sources.

At 601, the method includes receiving a position and a height of one or more sources. For example, the position and the height of the source may be received from a location awareness system. For example, the position of the source may be received from a GPS device.

At 603, the method includes receiving a position and a height of a gas sensor at a sensing location. For example, the position and the height of the gas sensor may be received from a location awareness system. For example, the position of the gas sensor may also be received from a GPS device. The method may further include determining the relative position of the sensor to each source in a geographic reference frame.

For a predetermined time interval 605, the method further includes, at 607, receiving a background concentration of the gas not affected by each source. The background concentration can be measured in multiple ways. For example, the background concentration can be obtained using satellite systems. The satellite can provide the background concentration rating for a particular area. In another embodiment, the background concentration can be received from another device (such as a gas detector, etc.). In a further embodiment, the background concentration can be measured in a location closed to the site and used in the method. In another embodiment, the background concentration can be measured at the site by a device at a time when the emission source is not emitting. In a further embodiment, the background concentration can be obtained when the emission source is emitting (for e.g., source location is north) and the background measurement is taken at a position (for e.g., a position south of the source location) not affected by the source emission and the wind (for e.g., the wind is blowing from south to north).

At 609, the method further includes receiving atmospheric stability information including atmospheric stability class information associated with the sensing location. Atmospheric stability may refer to a measure of atmospheric status which determines whether or not air will rise, sink, or be neutral. In general stability refers to air tendency to rise or to resist vertical motion (see, for example, Salby, M. L. (1996), *Fundamentals of atmospheric physics* (pp. 627 (4, 5 11, 14)), San Diego: Academic).

In one embodiment, atmospheric stability information relevant to the area being surveyed can be received from a third-party system, such as a weather network system or an airport system. Optionally, the third-party system can include a source of atmospheric meteorological information, especially wind direction, but also wind speed or atmospheric stability class, either on-board the system or at a nearby stationary location. As used herein, "nearby" means close enough that the atmospheric conditions at the location of the system are well-correlated to the stationary measurements.

In another embodiment, estimating the atmospheric stability class includes: (a) calculating the sunrise and sunset hour for the location and the time to determine whether it is day or night; (b) calculating the standard deviation of the wind direction. Wind direction is an angle, not a scalar, and its 360° periodicity is taken into account; (c) using the standard deviation, time of the day and the table from Mitchell and Timbre (see Mitchell, J. A., and K. Timbre, 1979: *Atmospheric stability class from horizontal wind fluctuation. Presented at 72nd Annual Meeting of Air Pollution Control Association, Cincinnati, OH; Jun.* 24-29, 1979, *Docket No. A*-80-46, II-P-9) to determine the stability class of the atmosphere. For example: if the standard deviation of the wind direction is 15° and it is daytime, then the stability class is "C". As will be appreciated by the skilled reader, the methods and systems disclosed herein may use any other suitable method for determining the atmospheric stability class.

At 611, the method includes determining dispersion parameters based at least on the atmospheric stability information. To estimate the dispersion parameters for each source and time t, the well-known equations derived by Turner (see Turner, D. B., 1970: *Workbook of atmospheric dispersion estimates/D. Bruce Turner. National Air Pollution Control Administration Cincinnati, Ohio, vii*, 84 p.) can be used. For example, the horizontal and vertical dispersion parameters are known as $\sigma_y$ and $\sigma_z$. For example: for a downwind distance of 36.4 m and a stability class of "C", the horizontal dispersion parameter is $\sigma_y$=4.88 m and the vertical dispersion parameter is $\sigma_z$=2.95 m. As will be appreciated by the skilled reader, the methods and systems disclosed herein may use any other suitable method for determining the dispersion parameters.

At 613, the method includes measuring a set of parameters, including: a concentration of the gas using the gas sensor, and a wind speed and wind direction. For example, the gas sensor can be used to measure the concentration of at least one type of gas at the sensing location The wind direction and wind speed can be measured by a wind measurement device as described in elsewhere the present disclosure. In some embodiments, this step may further include any of:

Transforming the wind direction from a clockwise (CW) from north measurement into a mathematical angle, counter clockwise (CCW) from the x (west from east) axis. For example, a N200 wind has a 250° direction in the mathematical plane.

Transforming the geographical coordinates (latitude, longitude) of the source and sensor into projected coordinates. For example, Universal Transverse Mercator (UTM) coordinates in meters can be used. The UTM zone is determined using the latitude and longitude of the sensor.

Calculating the distance to the source using the known locations. For example, assuming that the projected coordinates for the source are (2,7) and for the sensor (4, 45), then, the distance is:

$$d = \sqrt{(4-2)^2 + (45-7)^2} = 38(\text{Pythagor}).$$

Calculating the azimuth of the sensor in a polar reference frame centred on the source and with the wind direction as the reference direction. So, for each time t and each source, we have a different sensor location. Using the previous sensor and source locations and a wind direction at instant t of N200, the sensor azimuth is then:

$$\theta = [\text{Arg}((2-4) + i \times (7-45)) - 250 \times \pi / 180]_{2\pi} = 0.3 \text{ radian} = 17°,$$

$$\text{where } i = \sqrt{-1}.$$

Transforming the sensor polar coordinates (d, 0) into cartesian coordinates (x, y). Thus, for the previous example:

$$\begin{cases} x = \text{Re}(d \times e^{i \times \theta}) = 36.4 \\ y = \text{Im}(d \times e^{i \times \theta}) = 11.1 \end{cases}$$

At 615, the method includes repeating step 613 N times during the predetermined time interval to collect N sets of parameters.

At 617, the method includes inputting the N sets of parameters, the position and height of the at least one source, the position and height of the gas sensor, the background concentration of the gas not affected by the at least one source and the dispersion parameters into a function relating the gas concentration to the wind direction. For example, the function can be the modelled concentration (in µg/m3) at (x,y,z) for a continuous elevated point source located in (0,0,h) as described below.

Figures 4A, 4B, 4C, 5A, 5B, 5C:
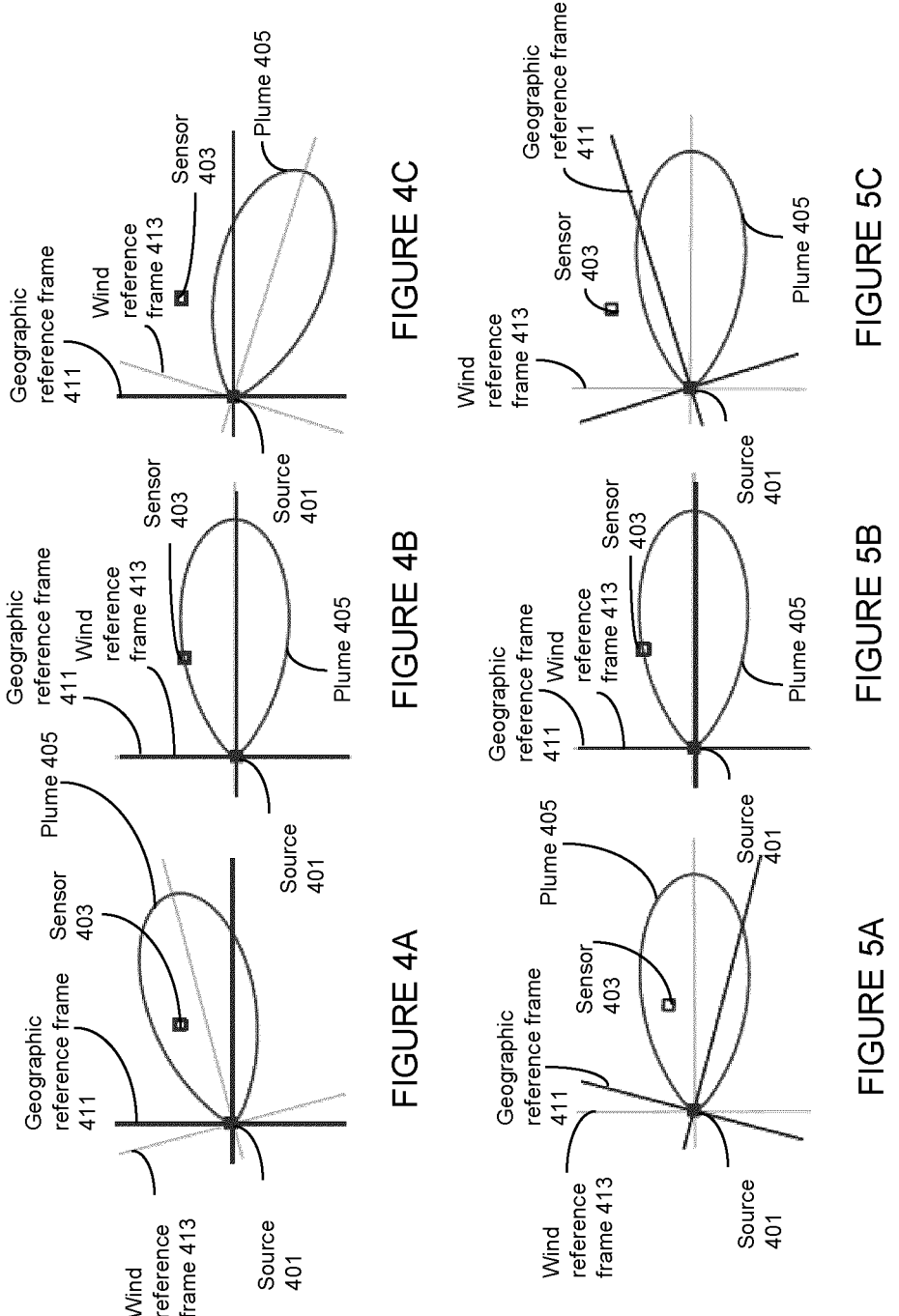
FIGS. 4A, 4B and 4C shows a diagram of a source, a stationary sensor and a moving plume according to one example.
FIGS. 5A, 5B and 5C shows a diagram of a source, a stationary plume and a moving sensor according to one example.

The method includes calculating a model concentration using the measured wind speed, the determined relative position of each of the at least one source with respect to the sensing location, the height of each source and the height of the sensor and the estimates of the dispersion parameters for each wind direction. To calculate the contribution of each source to the total mixing ratio using an emission rate of 1 m³/day for each at time t, the Gaussian plume dispersion model can be used. The Gaussian plume dispersion model does not have time dependence. Accordingly, the wind/ plume direction cannot change over time, though the model provides concentrations at all locations. The aim of this step is to transform the arrangement shown in FIGS. 4A, 4B and 4C (source 401, stationary sensor 403, moving plume 405, stationary geographic reference frame 411 and moving wind reference frame 413) into one that fits with the model requirements (stationary plume 405, moving sensor 403, moving geographic reference frame 411 and stationary wind reference frame 413).

For each source and time t, the input variables are the emission rate Q, the dispersion parameters, the wind speed u, the crosswind distance x, the downwind distance y, the height of the source h and the height of the sensor z. The model returns a mixing ratio at the sensor location.

Using a mathematical reference frame where the x axis is the downwind direction, the y axis the crosswind direction, and the z axis the vertical direction positive upward, the modelled concentration (in µg/m³) at (x,y,z) for a continuous elevated point source located in (0,0,h) is:

$$\chi(x, y, z) = \frac{Q}{2\pi\sigma_y\sigma_z u} \exp\left(-\frac{y^2}{2\sigma_y^2}\right) \times \left\{\exp\left[-\frac{(z-h)^2}{2\sigma_z^2}\right] + \exp\left[-\frac{(z+h)^2}{2\sigma_z^2}\right]\right\}$$

For example, the wind speed can be calculated as the median wind speed over the 20-minute-long intervals. In another embodiment, the wind speed can be calculated as a mean speed (or any other quantile representative of the wind speed) over a time interval (such as a 20-minute-long interval). It will be appreciated by the skilled reader that the interval may be of any suitable length of time.

The emission rate and the concentration can be expressed in the right units. For methane, a unitary Q=1 m³/day rate corresponds to 7851.5254 µg/s and a concentration of C=1 µg/m³ corresponds to a mixing ratio of 0.0014741179 parts per million by volume (ppmv) at a standard temperature of 288.15 K and atmospheric pressure of 1 Atm (units transformed using the ideal gas law).

For example: assuming the source is 2.5 m high, the sensor 2 m high and a median windspeed of 3.5 m/s and using the previously calculated variables uy, uz, y, a modelled mixing ratio of 0.003571504 ppmv can be found at the sensor location from a 1 m³/day source. The total mixing

13 ratio from all the known sources at instant t is the sum of each contribution. This results in a mixing ratio versus wind direction profile model.

At 619, the method further includes inverting the function relating the gas concentration to the wind direction to obtain each source emission rate. In this step, the following equation can be solved:

$$\text{total measured concentration} = \sum_{j=1}^{n} (\text{modelled concentration} \times \text{rate})_{source\,j}$$

On the left side of the above equation, for example, there can be 20 minutes of measurements (i.e., a 20-minute interval). If records are created at a frequency of 1 Hz, this would correspond to 1200 mixing ratio values. On the right side, there are n unknown rates (where n is the number of sources). In other words, there are 1200 linear equations of n unknown variables. When n<1200, the system of equation is overdetermined. To solve such a system, a linear least-square solver can be used.

For example, emissions rates can be solved using a linear squares method from computing the contribution of each source at each location for an emission rate of Q=1. In matrix form, this can be written as:

$$\chi = \begin{bmatrix} \chi_1 \\ \chi_2 \\ ... \\ \chi_n \end{bmatrix} = Q_1 \times \begin{bmatrix} c_{11} \\ c_{12} \\ ... \\ c_{1n} \end{bmatrix} + Q_2 \times \begin{bmatrix} c_{21} \\ c_{22} \\ ... \\ c_{2n} \end{bmatrix} + ... + Q_m \times \begin{bmatrix} c_{m1} \\ c_{m2} \\ ... \\ c_{mn} \end{bmatrix} \text{ or } \chi = qc$$

where $\chi$ is a vector of measured concentrations for wind directions 1, 2, . . . , n; q is a vector of point emission rates from source 1, 2, . . . , m; c is a n×m matrix of concentration from source 1 to m at a 1 g/s rate and for wind directions 1 to n.

The matrix solution can be represented by the following equation:

$$q = c^{-1} \chi$$

An extreme case would include a single measurement and a single source. In such a case, the standard deviation of the wind direction may not be determined, so it is assumed to be known. The Gaussian plume dispersion model represents an average concentration over a 10 min to 1 h time interval. Accordingly, assuming that the single measurement is representative of the average concentration at this location, a modelled mixing ratio corresponding to an emission rate of 1 m³/day can be calculated and the estimated emission rate is the enhanced mixing ratio divided by the modelled mixing ratio. No least-square solver is needed in that case because there is one equation of one unknown.

For example:
enhanced mixing ratio=10 ppmv
modelled mixing ratio=2 ppmv
then rate=10/2=5 m³/day.

If there are two measurements, then there are two equations of one unknown. Each equation might lead to a different emission rate, so it is possible to find the one for which the distance between the measured concentration and the product of the rates and the modelled concentration is minimal.

14

For example:
enhanced mixing ratio=10 ppmv and 13 ppmv
modelled mixing ratio=2 ppmv and 3 ppmv
then from the first equation, the rate is 10/2=5 m³/day and from the second equation, it is 13/3=4.3 m³/day.

There is not a unique solution in this case, so one can find the approximated rate $\overline{Q}$ (emission rate) for which:

$$\sum_{i=1}^{i=2} (\text{Modelled}_i \times Q - \text{Enhanced}_i)^2$$

is minimal:

$$\overline{Q} = \frac{\sum_{i=1}^{i=2} \text{Modelled}_i \times \text{Enhanced}_i}{\sum_{i=1}^{i=2} \text{Modelled}_i^2}.$$

In that case, a rate of 4.54 m³/day is found as the least square solution.

The least-square approach can be used for multiple sources as well. In that case, one can find $\overline{Q_j}$ that minimize:

$$\sum_{i=1}^{i=m} \sum_{j=1}^{j=n} (\text{Modelled}_{i,j} \times Q_j - \text{Enhanced}_{i,j})^2$$

where m is the number of observations (should be 1200) and n the number of sources.

Referring to FIG. 7, there is shown a method 700 for estimating emission rates of one or more sources according to another embodiment. The method 700 includes all the steps 601 to 619 of the method 600. Further, at 711, the method includes repeating the steps 605 to 619 for every new time interval.

Figure 8:
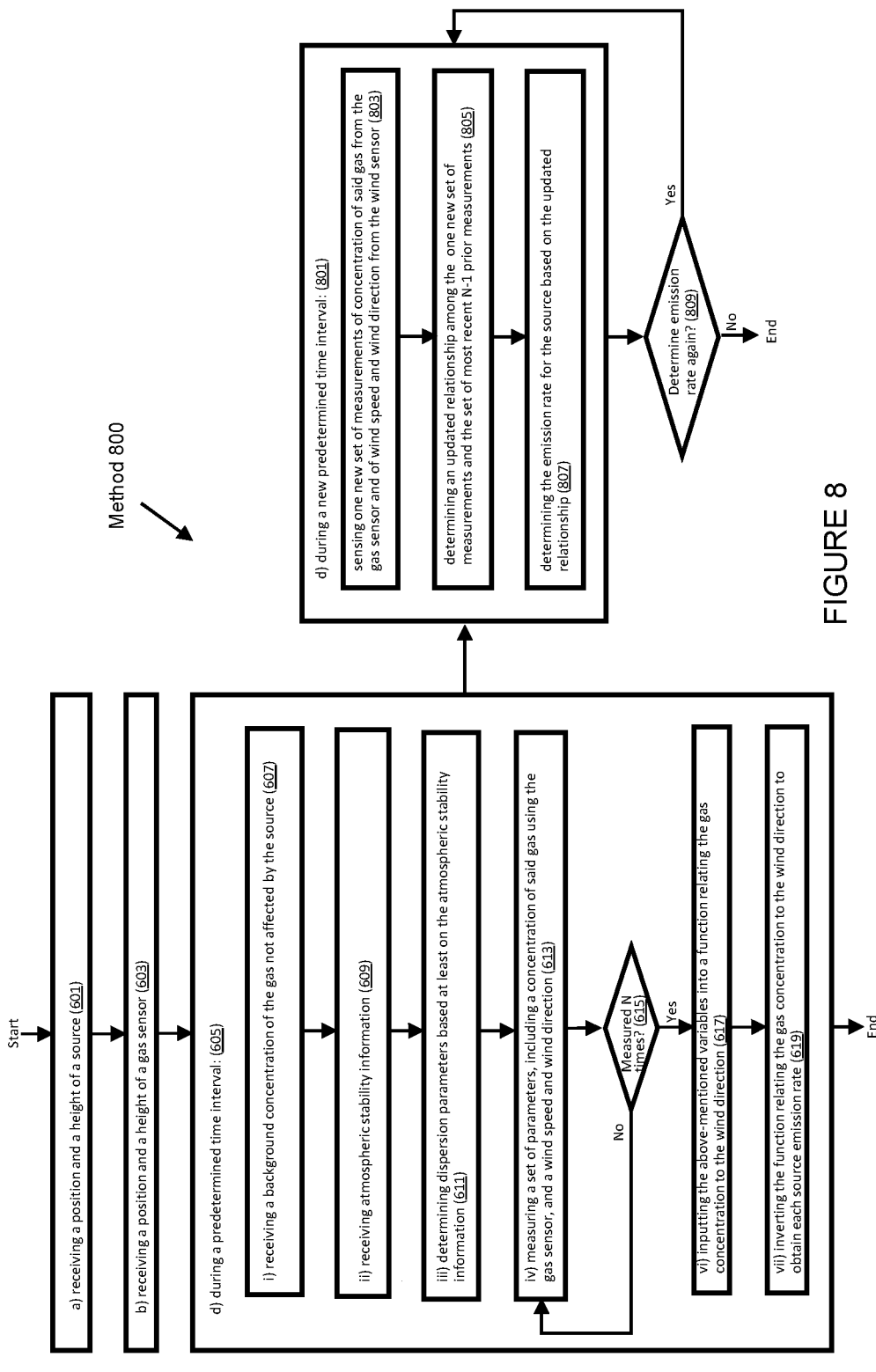
FIG. 8 shows a flowchart of a method for determining an emission rate according to a further example.

Referring to FIG. 8, there is shown a method 800 for estimating emission rates of one or more sources according to a further embodiment. The method 800 includes all the steps 601 to 619 of the method 600. Further, during a new predetermined time interval 801, the method includes, at 803, repeating step 613 to measure a new set of parameters.

At 805, the method includes inputting the new set of parameters, N−1 most recent prior sets of parameters, the position and height of the at least one source, the position and height of the inlet of the gas sensor, the background concentration of the gas not affected by the at least one source and the dispersion parameters into the function relating the gas concentration to the wind direction as previously defined. At 807, the method includes inverting the function relating the gas concentration to the wind direction to obtain each source new emission rate. At 809, the method includes determining whether to compute a new emission rate. If yes, the method includes repeating the steps 803 to 807 for a new time interval.

For example, the method further includes receiving the position and the height of each source and the position and the height of the gas sensor by using a location awareness system. The position and the height of the source can be received from a GPS device. The position of the gas sensor can also be received from a GPS device.

The method can use a linear solver to invert the function relating the gas concentration to the wind direction. The linear solver can be a linear least-square solver.

For example, the method further includes measuring the wind speed and the wind direction using a wind sensor. The wind sensor can be an anemometer. The method can include determining the direction of the anemometer.

A system for estimating an emission rate of at least one source is provided in the present disclosure. The system includes an anemometer for gauging wind direction and a wind speed, a gas sensor for measuring concentration of a gas, and a processor coupled to the wind sensor and the gas sensor. The processor configured to receive a position and a height of the at least one source and receive a position and a height of the gas sensor at a sensing location. The processor is further configured to, during a predetermined time interval: i) receive a background concentration of the gas not affected by the at least one source; ii) receive atmospheric stability information associated with the sensing location; iii) determine dispersion parameters based at least on the atmospheric stability information; iv) measure a set of parameters, including a concentration of the gas using the gas sensor, and a wind speed and wind direction using the wind sensor; v) repeat step iv) N times during the interval to collect N sets of parameters; vi) input the N sets of parameters, the position and height of the at least one source, the position and height of the gas sensor, the background concentration of the gas not affected by the at least one source and the dispersion parameters into a function relating the gas concentration to the wind direction; and vii) invert the function relating the gas concentration to the wind direction to obtain each source emission rate.

For example, the processor is further configured to repeat the steps i) to vii) for plurality of time intervals.

For example, the processor is further configured to: repeat step iv) to measure a new set of parameters; input the new set of parameters, N−1 most recent prior sets of parameters, the position and height of the at least one source, the position and height of the inlet of the gas sensor, the background concentration of the gas not affected by the at least one source and the dispersion parameters into the function relating the gas concentration to the wind direction; and invert the function relating the gas concentration to the wind direction to obtain each source new emission rate.

For example, the processor is further configured to receive the position and the height of the at least one source and the position and the height of the gas sensor from a location awareness system. The processor can be configured to invert the function relating the gas concentration to the wind direction by using a linear solver. The linear solver can include a linear least-square solver. The position and the height of each source can be received from a GPS device. The position of the gas sensor can be received from a GPS device.

The processor can be configured to receive the position and the height of an inlet of the gas sensor, wherein the gas sensor is adapted to receive, through the inlet into a chamber, ambient air containing the gas at the sensing location, and measure concentration of the gas inside the chamber.

In a further embodiment, the method includes determining a location of one or more sources using a Lagrangian particle dispersion model. In particular, this method uses Lagrangian back-trajectory analysis, which maps out probabilities of an emission source across the landscape. Normally, Lagrangian probability maps are interpreted by eye.

The inventors have developed a new automated method to recover source locations using a Lagrangian dispersion model. The measured wind vectors and gas concentrations are processed to produce a concentration footprint map for the area of interest. The model also requires information relating to the sensing location, the type of landscape and a measure of the atmospheric stability. The wind vectors are rotated so that the main wind direction is Eastward/N270. That way the footprint x-axis is parallel to the downwind direction.

The footprint map is then investigated using the computer-implemented method set out below, which looks for monotonous increases in the x and y directions of the footprint map. Lengths of increase are explored from a length of one to a length equal to the smallest dimension of the grid. Each grid cell is attributed the longest increase length. These grid cell values are then weighted using the magnitude of the concentration footprint before being mapped to reveal the potential locations of the emitting sources as the local maxima of the grid. These can be single locations or areas of potential locations.

These potential locations are filtered to only keep the ones that are upwind and in the field of view of the sensor, and then converted into geographic locations by rotating the xy-frame so that the wind vector is back to its original direction.

In a further embodiment, a location awareness system can be used to determine the respective locations and distances between the sensors (e.g., wind measurement devices, gas sensing devices, etc.) and the emission sources. The relative azimuth of the sensor to each source can also be determined. Different systems may be used for location awareness. A LIDAR system may also be used to determine the relative locations of the sensors and the emission sources. For example, the LIDAR system can include sensors that capture information (or data) that describes the location of the sensors and the emission sources within a surrounding environment. For example, the LIDAR sensors can be mounted on a vehicle operable to move within an industrial site. The vehicle may be a land-based vehicle, such as a car, truck, all-terrain vehicle, motorcycle, snowmobile, etc. The vehicle may also be an air-based vehicle, such as a plane, helicopter, drone or unmanned aerial vehicle (UAV).

It should be appreciated that the methodologies described herein, including flow charts, diagrams and accompanying disclosure can be implemented using computer system 801 as a standalone device or on a distributed network of shared computer processing resources such as a cloud computing network.

The description and drawings merely illustrate the principles of the invention. It will thus be appreciated that those skilled in the art will be able to devise various arrangements that, although not explicitly described or shown herein, embody the principles of the invention and are included within the scope of the appended claims. Furthermore, all examples recited herein are principally intended expressly to be only for pedagogical purposes to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention, as well as specific examples thereof, are intended to encompass equivalents thereof.

The functions of the various elements shown in FIG. 1, including the functional block labelled as "processor", may be provided through the use of dedicated hardware as well as hardware capable of executing software in association with appropriate software. When provided by a processor, the functions may be provided by a single dedicated processor, by a single shared processor, or by a plurality of individual processors, some of which may be shared. Moreover, explicit use of the term "processor" should not be construed to refer exclusively to hardware capable of executing software, and may implicitly include, without limitation, digital signal processor (DSP) hardware, network processor, application specific integrated circuit (ASIC), field programmable gate array (FPGA), read only memory (ROM) for storing software, random access memory (RAM), and non-volatile storage. Other hardware, conventional and/or custom, may also be included.

It should be appreciated by those skilled in the art that any block diagrams herein represent conceptual views of illustrative software and/or circuitry embodying the principles of the invention. Similarly, it will be appreciated that any flow charts, flow diagrams, state transition diagrams, pseudo code, and the like represent various processes which may be substantially represented in computer readable medium and so executed by a computer or processor whether or not such computer or processor is explicitly shown.

The invention claimed is:

1. A method for estimating an emission rate of at least one source, comprising:
    a) receiving a position and a height of the at least one source;
    b) receiving a position and a height of a gas sensor at a sensing location;
    c) during a predetermined time interval:
        i) receiving a background concentration of the gas not affected by the at least one source;
        ii) receiving atmospheric stability information associated with the sensing location;
        iii) determining dispersion parameters based at least on the atmospheric stability information;
        iv) measuring a set of parameters, including:
            a concentration of said gas using the gas sensor, and
            a wind speed and wind direction;
        v) repeating step iv) N times during the predetermined time interval to collect N sets of parameters;
        vi) inputting the N sets of parameters, the position and height of the at least one source, the position and height of the gas sensor, the background concentration of the gas not affected by the at least one source and the dispersion parameters into a function relating the gas concentration to the wind direction; and
        vii) inverting the function relating the gas concentration to the wind direction to obtain each source emission rate.

2. The method of claim 1, comprising repeating the steps i) to vii) for plurality of time intervals.

3. The method of claim 1, further comprising:
    repeating step iv) to measure a new set of parameters;
    inputting the new set of parameters, N−1 most recent prior sets of parameters, the position and height of the at least one source, the position and height of the inlet of the gas sensor, the background concentration of the gas not affected by the at least one source and the dispersion parameters into the function relating the gas concentration to the wind direction; and
    inverting the function relating the gas concentration to the wind direction to obtain each source new emission rate.

4. The method of claim 1, further comprising receiving the position and the height of the at least one source and the position and the height of the gas sensor by using a location awareness system.

5. The method of claim 1, comprising using a linear solver to invert the function relating the gas concentration to the wind direction.

6. The method of claim 5, wherein the linear solver comprises a linear least-square solver.

7. The method of claim 1, further comprising measuring the wind speed and the wind direction using a wind sensor.

8. The method of claim 7, wherein the wind sensor comprises an anemometer.

9. The method of claim 8, further comprising determining the direction of the anemometer.

10. The method of claim 1, wherein the position and the height of the at least one source is received from a GPS device.

11. The method of claim 1, wherein the position of the gas sensor is received from a GPS device.

12. The method of claim 1, wherein receiving the position and the height of the gas sensor comprises receiving the position and the height of an inlet of the gas sensor, wherein the gas sensor is adapted to receive, through the inlet into a chamber, ambient air containing the gas at the sensing location, and measure concentration of said gas inside the chamber.

13. A system for estimating an emission rate of at least one source, comprising:
    an anemometer for gauging wind direction and a wind speed;
    a gas sensor for measuring concentration of a gas; and
    a processor coupled to the wind sensor and the gas sensor, the processor configured to:
        a) receive a position and a height of the at least one source;
        b) receive a position and a height of the gas sensor at a sensing location;
        c) during a predetermined time interval:
            i) receive a background concentration of the gas not affected by the at least one source;
            ii) receive atmospheric stability information associated with the sensing location;
            vii) determine dispersion parameters based at least on the atmospheric stability information;
            iv) measure a set of parameters, including:
                a concentration of said gas using the gas sensor, and
                a wind speed and wind direction using the wind sensor;
            v) repeat step iv) N times during the interval to collect N sets of parameters;
            vi) input the N sets of parameters, the position and height of the at least one source, the position and height of the gas sensor, the background concentration of the gas not affected by the at least one source and the dispersion parameters into a function relating the gas concentration to the wind direction; and
            vii) invert the function relating the gas concentration to the wind direction to obtain each source emission rate.

14. The system of claim 13, wherein the processor is further configured to repeat the steps i) to vii) for plurality of time intervals.

15. The system of claim 13, wherein the processor is further configured to: repeat step iv) to measure a new set of parameters;
    input the new set of parameters, N−1 most recent prior sets of parameters, the position and height of the at least one source, the position and height of the inlet of the gas sensor, the background concentration of the gas not affected by the at least one source and the dispersion parameters into the function relating the gas concentration to the wind direction; and invert the function relating the gas concentration to the wind direction to obtain each source new emission rate.

16. The system of claim 13, wherein the processor is further configured to receive the position and the height of the at least one source and the position and the height of the gas sensor from a location awareness system.

17. The system of claim 13, wherein the processor is configured to invert the function relating the gas concentration to the wind direction by using a linear solver.

18. The system of claim 17, wherein the linear solver comprises a linear least-square solver.

19. The system of claim 18, wherein the position and the height of the at least one source is received from a GPS device.

20. The system of claim 13, wherein the processor is configured to receive the position and the height of an inlet of the gas sensor, and wherein the gas sensor is adapted to receive, through the inlet into a chamber, ambient air containing the gas at the sensing location, and measure concentration of said gas inside the chamber.

* * * * *